United States Patent [19]

Greczyn et al.

[11] Patent Number: 5,354,553
[45] Date of Patent: Oct. 11, 1994

[54] ANTIPERSPIRANT-DEODORANT COSMETIC STICK PRODUCTS

[75] Inventors: Wendy R. Greczyn, Randolph; M. Stephen Lajoie, Basking Ridge; John R. Berschied, Lawrenceville; Lawrence Kirschner, Flanders, all of N.J.

[73] Assignee: Church & Dwight Co., Inc, Princeton, N.J.

[21] Appl. No.: 986,916

[22] Filed: Dec. 8, 1992

[51] Int. Cl.⁵ .................. A61K 7/32; A61K 7/34; A61K 7/38; A61K 9/14
[52] U.S. Cl. ........................... 424/65; 424/66; 424/68; 424/DIG. 5; 424/401; 424/493; 424/497
[58] Field of Search ............ 424/65, 66, 67, 68, 424/DIG. 5, 401, 486, 493, 497

[56] References Cited

U.S. PATENT DOCUMENTS 4,673,570  6/1987  Soldati ............................ 424/66
4,832,945  5/1989  Osipow et al. ................... 424/65

OTHER PUBLICATIONS

Remington's Pharmaceutical Sciences. 15th ed. pp. 1604–1605. Mack Publishing Co., Pa. (1975).

Primary Examiner—Marianne M. Cintins
Assistant Examiner—Phyllis G. Spivack
Attorney, Agent, or Firm—Charles B. Barris

[57] ABSTRACT

This invention provides an improved process for producing an antiperspirant-deodorant cosmetic stick product. An essential aspect of the process improvement is a phased order of ingredient addition and blending of formulation ingredients under controlled temperature conditions. Another essential aspect is the incorporation of particulate antiperspirant and alkali metal bicarbonate ingredients, at least one of which has ingredient particle surfaces coated with a hydrophilic organic polymer.

30 Claims, No Drawings

ANTIPERSPIRANT-DEODORANT COSMETIC STICK PRODUCTS

CROSS-REFERENCE TO RELATED PATENT APPLICATIONS

The subject matter of the present invention is related to that described in patent application Ser. No. 986,917, filed Dec. 8, 1992; and patent application Ser. No. 986,810, filed Dec. 8, 1992.

BACKGROUND OF THE INVENTION

Antiperspirants combat axillary odors by inhibiting perspiration through the action of astringent salts such as aluminum and zinc salts, but may be irritating to a large number of users. Deodorants function by neutralizing the objectionable odors resulting from the degradation of several components of perspiration by chemical and microbial action into malodorous fatty acids.

Numerous solid antiperspirant and/or deodorant compositions have been described in the chemical and cosmetic literature. These compositions generally are emulsion sticks or suspensoid sticks. Emulsion sticks contain a solution of the antiperspirant ingredient incorporated into the stick via an emulsion. Although emulsion sticks are desirable in certain respects, they tend to be unstable, exhibit tackiness, and leave a visible residue on the skin after use. Suspensoid sticks contain the powdered antiperspirant ingredient suspended in the stick without the use of water or an emulsion. While suspensoids have stability, they tend to leave a white chalky residue on the skin after application.

Manufacturers have found that anhydrous antiperspirant stick systems are more marketable and have good consumer acceptance primarily due to the ease of application to the skin, good cosmetic esthetics and an acceptable degree of effectiveness. Previous to the development of anhydrous stick systems, numerous water based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin, and their consistency and effectiveness are variable.

Many anhydrous stick compositions have been described in the literature which attempt to improve the delivery and the effectiveness of their antiperspirant and deodorant characteristics. Antiperspirant stick systems consisting of low molecular weight monohydric alcohols in conjunction with polyhydric alcohols are described in U.S. Pat. No. 4,137,306. These sticks have the advantage of quicker drying rates, but the residue of the polyhydric alcohols in combination with the astringent salts produces a high degree of tack, and their effectiveness is limited to the type and amount of astringent salts that could be incorporated in the stick matrix.

Anhydrous stick compositions that suspend the aluminum salt in a hydrophobic matrix are described in U.S. Pat. No. 4,049,792. These compositions employ waxy materials and long chain fatty esters to form a stick that delivers the active astringent salts to the skin. Cosmetic stick compositions made in accordance with these embodiments are greasy, and the active astringent salt is enveloped in a manner that prevents maximum performance. To alleviate this inherent negative characteristic, volatile silicone fluids replacement of the less volatile long chain fatty esters is described in U.S. Pat. No. 4,126,679. This disclosure teaches the advantage of utilizing a volatile non-staining liquid such as cyclic dimethylpolysiloxanes (referred to as volatile silicones), in combination with various types of waxes, as a carrier for the active astringent salts in an antiperspirant stick composition. Similar antiperspirant stick compositions containing volatile silicones are described in U.S. Pat. Nos. 4,511,554; 4,980,156; and 4,985,238.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. Nos. 4,822,602 and 4,832,945.

However, the development of a practical and effective antiperspirant composition in cosmetic stick form which is also capable of deodorization, and which is capable of consumer acceptability, presents many factors which are unique. Because sodium and potassium bicarbonate have only limited solubility in water, alcohol and other solvents, the preparation of a composition suitable for dispensing in cosmetic stick form has involved many processing obstacles. In addition to the problem of limited solubility, sodium bicarbonate is incompatible with the active astringent salts and with other ingredients of conventional stick compositions. Also, the dimensional stability of the cosmetic stick containing sodium bicarbonate, and the esthetic appearance and the "feel" on the skin, are just a few of the additional difficulties encountered in the preparation of a low residue antiperspirant-deodorant cosmetic stick product.

Another problem associated with the incorporation of a bicarbonate deodorant ingredient in an antiperspirant formulation is the tendency for the high density bicarbonate salt particles to settle in the fluid medium during processing. Also, under the elevated temperature conditions required for the admixing and blending of ingredients, bicarbonate degradation and evolution of carbon dioxide and water occur.

There is continuing interest in the development of antiperspirant cosmetic stick products which exhibit deodorizing activity, and in improved processes for their preparation.

Accordingly, it is an object of this invention to provide a process for the manufacture of an antiperspirant-deodorant cosmetic stick product which contains a bicarbonate deodorant ingredient, and which is characterized by excellent esthetics and cosmetic properties.

It is another object of this invention to provide a homogeneous antiperspirant cosmetic stick product containing a bicarbonate deodorant ingredient which is a particulate solid having particles with an organic polymeric coating that lowers the relative density of the particles.

Other objects and advantages of the present invention shall become apparent from the accompanying description and examples.

DESCRIPTION OF THE INVENTION

One or more objects of the present invention are accomplished by the provision of a process for preparing an antiperspirant-deodorant cosmetic stick product which comprises (1) heating between about 10–50 parts by weight of a volatile silicone oil ingredient to a temperature of about 120°-220° F.; (2) adding to the heated silicone oil ingredient between about 1-30 parts by weight of a liquid emollient ingredient, between about 12-24 parts by weight of a low melting point wax ingredient, and between about 0.5-5 parts by weight of a surfactant ingredient to form a homogeneous fluid medium; (3) adding between about 18-30 parts by weight of an antiperspirant ingredient to the heated fluid medium; (4) adding between about 0.05-30 parts by weight of a particulate alkali metal bicarbonate deodorant ingredient to form a homogeneous fluid suspension medium, wherein the surfaces of the added alkali metal bicarbonate particles are pre-coated with a hydrophilic organic polymer; and (6) dispensing the heated fluid suspension medium into cosmetic stick containers, and cooling the container contents to form solid sticks at room temperature.

In another process embodiment, particulate antiperspirant ingredient has particles pre-coated with a hydrophilic polymer to prevent interaction with basic ingredients and to minimize settling during processing or in the final cosmetic stick product. Optionally, both the particulate antiperspirant and alkali metal bicarbonate ingredients can be pre-coated with a hydrophilic polymer, which functions to protect the ingredient particles and to minimize settling because the density of the particles is decreased by the organic coating content.

An invention antiperspirant-deodorant cosmetic stick product typically contains the following weight proportions of main ingredients:

| Ingredient | Weight |
|---|---|
| volatile silicone oil | 25-50 |
| liquid emollient | 2-20 |
| wax (MP 95°-180° F.) | 15-20 |
| antiperspirant | 20-28 |
| bicarbonate deodorant | 0.1-25 |
| surfactant | 1-3 |

The volatile silicone oil ingredient in an antiperspirant-deodorant cosmetic stick product of the present invention preferably is a cyclic or linear polydimethylsiloxane containing between about 3-9 silicon atoms. A suitable cyclic volatile polydimethylsiloxane compound is illustrated by the formula:

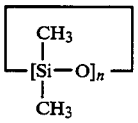

where n is an integer with a value of about 3-7.

A suitable linear polydimethylsiloxane is illustrated by the formula:

(CH$_3$)$_3$Si—O[Si(CH$_3$)$_2$—O]$_n$—Si(CH$_3$)$_3$ where n is an integer with a value of about 1-7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3-6. Dow Corning 245 Fluid (Dow Corning) is a cyclic volatile silicone which is commercially available. *CTFA Cosmetic Ingredient Dictionary*, Third Edition, (Estrin et al., Editors; The Cosmetic, Toiletry and Fragrance Association, Inc.; 1982) lists cyclic silicones on page 60, under the entry "Cyclomethicone".

The liquid emollient ingredient of an invention cosmetic stick product is selected from one or more water-insoluble organic compounds which are liquid at 25° C. and which contribute a combination of properties that are advantageous in an invention antiperspirant-deodorant cosmetic stick product.

The term "water-insoluble" as employed herein refers to an emollient ingredient which has a water-solubility of less than about one gram per 100 grams of water at 25° C.

A present invention emollient ingredient exhibits a low degree of irritation and toxicity in topical applications, and provides a softening or soothing effect on surface skin tissue.

Preferred water-insoluble liquid emollients include fatty acids such as oleic and ricinoleic; fatty alcohols such as oleyl, lauryl and hexadecyl; esters such as diisopropyl adipate, benzoic acid esters of C$_9$-C$_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic stick product comprises one or more organic compounds which have a melting point in the range between about 95°-180° F.

Suitable types of wax-like compounds include fatty acids, fatty alcohols, fatty acid esters, fatty acid amides, and the like, which have an aliphatic chain length between about 8-30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°-220° F. Illustrative of these higher melting waxes are beeswax, spermaceti, carnauba, bayberry, candelilla,, montan, ozokerite, ceresin, paraffin, castor wax, Fischer-Tropsch waxes, and the like.

The antiperspirant ingredient of a present invention cosmetic stick product typically is a particulate astringent compound which has an average particle size between about 1-100 microns. Superior cosmetic stick properties are obtained if part or all of the antiperspirant ingredient is in the form of particles which have a diameter less than about one micron.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum zirconium tetrachlorohydrex glycine which is commercially available as Rezal 36 GP Superultrafine (Reheis), and Reach AZP 908 (Reheis).

The bicarbonate deodorant ingredient of an invention cosmetic stick product is selected from alkali metal and ammonium bicarbonates, such as sodium bicarbonate, potassium bicarbonate and ammonium bicarbonate, and mixtures thereof. The bicarbonate deodorant ingredient can contain up to about 30 weight percent, based on the weight of deodorant ingredient, of an alkali metal or ammonium carbonate compound.

The average particle size of the bicarbonate deodorant ingredient can be in the range between about 1-100 microns. In formulations in which the bicarbonate deodorant ingredient particles are not surface-coated, improved cosmetic stick properties are obtained if part or all of the bicarbonate ingredient has a particle size diameter less than about one micron. Colloidal size particles facilitate incorporation into the cosmetic stick matrix, and the resultant stick composition has a smoother non-gritty feel when applied to the skin.

If the particulate bicarbonate deodorant ingredient is surface-coated with a hydrophilic polymer, the average size of the core bicarbonate particles typically is in the range between about 5-80 microns.

The surfactant ingredient of an invention cosmetic stick product is selected from nonionic, cationic and anionic polymers.

Suitable surfactant polymers include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

Optional ingredients also may be included in an invention cosmetic stick formulation, such as bacteriostats, fungistats, fillers, stabilizing agents, antioxidants, pigments, coloring agents, perfumes, hardeners, chelating agents, and the like.

A bacteriostat such as 2,4,4'-trichloro-2'-hydroxydiphenyl ether (Triclosan) typically is added in a quantity between about 0.08-3 weight percent, based on the weight of the cosmetic stick product.

An optional ingredient such as colloidal silica suspending agent is added in a quantity between about 1-3 weight percent, based on the weight of the cosmetic stick product.

An important aspect of the present invention is the utilization of pre-coated particles of alkali metal bicarbonate ingredient and/or antiperspirant ingredient in the manufacture of the antiperspirant-deodorant cosmetic stick product. The polymeric coating on one or both of the particulate antiperspirant and bicarbonate ingredient solid phases minimizes any reaction between the acidic and basic compounds, and prevents loss of antiperspirant-deodorant activities.

Pre-coating of ingredient particles also has the beneficial effect of improving the suspension properties of the particles in the fluid formulation admixture during processing. Less inorganic particle settling occurs because the density of the coated particles and the fluid formulation organic phase density are more closely matched than is the case with uncoated inorganic particles.

The application of the coating to the core matrix particles is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the individual particles.

The coating thickness on the particle surfaces typically will vary in the range between about 0.1-20 microns. The coating can consist of a single layer or multiple layers. The polymeric coating can constitute between about 5-30 weight percent of the total dry weight of the coated particles.

The hydrophilic polymer employed for coating the ingredient particles is selected from water-soluble and water-dispersible organic polymers. A mixture of polymers can be employed, and a content of between about 0.5-40 weight percent of a water-insoluble polymer, based on the coating weight, can be included.

The term "hydrophilic" as employed herein refers to an organic polymer which has a water-solubility of at least about one gram per 100 grams of water at 25° C.

Suitable hydrophilic polymers for coating particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, polydextrose, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of the coating.

The rate of particle matrix compound release from the particle core under moisture conditions can be controlled by the quantity and type of hydrophilic polymer coating on the particle surfaces.

Low molecular weight hydrophilic polymers will release the particle matrix compound at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release particle matrix compound at a relatively fast rate. Polyethylene oxide (M.W. of 4,000,000) or partially hydrolyzed polyvinyl acetate will release at a relatively slow rate. Polyvinylpyrrolidone will release particle matrix compound at an immediate rate when in contact with underarm type of moisture.

In general, the ingredients of the formulation can be blended in any order. However, as described hereinabove, in the practice of the invention process there is advantage in utilizing a phased order of ingredient addition and blending under controlled temperature conditions. Additional advantage is obtained in the invention process if there is a short time lapse between the alkali metal bicarbonate deodorant ingredient addition step and the cosmetic stick container filling and solidifying step. Alkali metal bicarbonate can convert to alkali metal carbonate, carbon dioxide and water at elevated temperatures.

Adding the bicarbonate deodorant as the last ingredient of the blended formulation, and processing the formulation to the solid cosmetic stick formation stage within a short time period, are factors which minimize the degradation of the bicarbonate ingredient, and the undesirable formation of water and carbon dioxide vapor byproducts. The addition and mixing of the bicarbonate deodorant ingredient into the formulation, and the dispensing of the formulation into cosmetic stick containers, can be accomplished as an essentially instantaneous procedure by utilizing an integrated mixing valve nozzle device, such as the type described in U.S. Pat. Nos. 2,816,518; 3,454,198; 3,949,904; 4,318,429; 4,549,813; 5,046,538; 5,094,276; and the like.

The practice of the invention process for the production of a cosmetic stick product can be conducted in conventional equipment, and is readily adaptable to a commercial-scale manufacturing operation.

A present invention cosmetic stick product preferably has a hardness penetration value between about 4–12 millimeters, as determined by American Society For Testing Materials (ASTM) Method D5.

A present invention antiperspirant-deodorant cosmetic stick product has exceptional properties for treating or preventing perspiration and malodor associated with human underarm perspiration. A present invention cosmetic stick product can be applied effectively with safety and comfort for reduction of underarm perspiration and offensive odors.

Because of the incorporation of the alkali metal bicarbonate deodorant ingredient and/or the antiperspirant ingredient in the form of polymer-coated particles, an invention cosmetic stick product has improved dimensional stability, and better esthetic appearance and "feel" when applied to human skin.

The following Examples are further illustrative of the present invention. The components and specific ingredients are presented as being typical and various modifications can be derived in view of the foregoing disclosure within the scope of the invention.

EXAMPLE I

This Example illustrates a procedure for coating a particulate bicarbonate deodorant compound with a water-soluble organic polymer in accordance with the present invention.

Guar gum (15 g, Supercol, Aqualon Co.) is dissolved in 150 ml of 50% aqueous ethanol solvent. Sodium bicarbonate (100 g, 50–80 microns, Church & Dwight) is suspended in the solution medium with stirring.

The solvent medium is removed by evaporation under vacuum. A dry free-flowing powder is obtained. The particles are coated with a guar film having an average thickness of 2–5 microns.

EXAMPLE II

This Example illustrates a fluidized bed procedure for coating an antiperspirant compound with a water-soluble polymer in accordance with the present invention.

A fluidized bed vessel is utilized which is equipped with a Wurster air-suspension coater system (WARF) as described in U.S. Pat. Nos. 4,568,559 and 4,877,621.

A coating solution is prepared by dissolving polyethylene glycol (45 g, Poly-G 2000, Olin Corp.), and propylene glycol butyl ether (10 g, PPG 14, Americol) in ethanol (600 g).

Particulate aluminum zirconium tetrachlorohydrex glycine (600 g, 60–100 microns, Reheis) is charged into the coating chamber.

Compressed air is introduced into the coating chamber, and the polymeric coating solution is sprayed on the air-suspended antiperspirant core matrix particles, until the coating weight is about 20% of the total dry weight of the coated particles.

The procedure is repeated, except that Hydroxypropylmethylcellulose (Methocel 60 HG, Dow Chemical Co.) is employed as the water-soluble polymer.

EXAMPLE III

This example illustrates a pilot-plant procedure for the preparation of an antiperspirant-deodorant cosmetic stick product in accordance with the present invention.

A stainless steel tank is provided which is equipped with turbine agitation.

Silicone oil DC 245 (600 lbs, Dow Corning) is charged to the mixing tank. Agitation (55–65 RPM) is initiated, and heating the liquid medium to 176° F. is commenced.

During the heating period, the following order of ingredients are added to the stirred liquid medium:

|  | lbs. |
| --- | --- |
| diisopropyl adipate | 60 |
| PPG 14 butyl ether (Americol) | 40 |
| stearyl alcohol | 340 |
| castor wax (MP-70) | 60 |
| eicosanol | 10 |
| PEG 600 distearate (Mazer) | 40 |

The mixture is stirred at 176° F. for about 30 minutes until the ingredients are melted and the liquid medium is homogeneous. The stirring speed is reduced to about 35 RPM, then Cab-o-sil M-5 (15 lbs, Cabot) and aluminum zirconium tetrachlorohydrex glycine (480 lbs, Reheis) are added. The temperature is maintained at 176° F. for about 40 minutes until the fluid medium is uniform, and then the temperature is lowered to 124° F.

Polymer-coated sodium bicarbonate 3 DF (140 lbs, Church & Dwight) and a fragrance (6 lbs, 1FF 567-AT) respectively are added with stirring to Silicone oil DC 245 (245 lbs, Dow Corning) in a second mixing tank at a temperature of 124° F. to form a homogeneous suspension medium. The sodium bicarbonate particles are pre-coated with guar gum as described in Example I.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

What is claimed is:

1. A process for preparing an antiperspirant-deodorant cosmetic stick product which comprises (1) heating between about 10–50 parts by weight of a volatile silicone oil ingredient to a temperature of about 120°–220° F.; (2) adding to the heated silicone oil ingredient between about 1–30 parts by weight of a liquid emollient ingredient, between about 12–24 parts by weight of a low melting point wax ingredient, and between about 0.5–5 parts by weight of a surfactant ingredient to form a homogeneous fluid medium; (3) adding between about 18–30 parts by weight of an antiperspirant ingredient to the heated fluid medium; (4) adding between about 0.05–30 parts by weight of a particulate alkali metal bicarbonate deodorant ingredient to form a homogeneous fluid suspension medium, wherein the surfaces of the added alkali metal bicarbonate particles are pre-coated with a hydrophilic organic polymer; and (5) dispensing the heated fluid suspension medium into cosmetic stick containers, and cooling the container contents to form solid sticks at room temperature.

2. A process in accordance with claim 1 wherein the volatile silicone oil ingredient comprises between about 25–50 weight percent of the cosmetic stick product.

3. A process in accordance with claim 1 wherein the volatile silicone oil ingredient comprises a cyclic or linear polydimethylsiloxane containing 3–9 silicon atoms.

4. A process in accordance with claim 1 wherein the liquid emollient ingredient comprises between about 2–20 weight percent of the cosmetic stick product.

5. A process in accordance with claim 1 wherein the liquid emollient ingredient is a water-insoluble organic acid, ester or ether compound.

6. A process in accordance with claim 1 wherein the liquid emollient ingredient is diisopropyl adipate.

7. A process in accordance with claim 1 wherein the wax ingredient has a melting point in the range of about 95°–180° F., and comprises between about 15–20 weight percent of the cosmetic stick product.

8. A process in accordance with claim 1 wherein the wax ingredient is selected from $C_8$–$C_{30}$ alcohol, acid, ester and amide compounds.

9. A process in accordance with claim 1 wherein the wax ingredient comprises stearyl alcohol or castor wax or a mixture thereof.

10. A process in accordance with claim 1 wherein the surfactant ingredient comprises between about 1–3 weight percent of the cosmetic stick product.

11. A process in accordance with claim 1 wherein the surfactant ingredient is selected from nonionic, cationic and anionic polymers.

12. A process in accordance with claim 1 wherein the surfactant ingredient is polyalkylene glycol diester.

13. A process in accordance with claim 1 wherein the antiperspirant ingredient comprises between about 20–28 weight percent of the cosmetic stick product, and is a particulate solid having an average particle size between about 1–100 microns.

14. A process in accordance with claim 1 wherein the antiperspirant ingredient is selected from astringent aluminum and zirconium compounds, and complexes or mixtures thereof.

15. A process in accordance with claim 1 wherein the antiperspirant ingredient is an aluminum-zirconium tetrachlorohydrate compound.

16. A process in accordance with claim 1 wherein the deodorant ingredient comprises between about 0.1–25 weight percent of the cosmetic stick product, and is a particulate alkali metal bicarbonate solid having an average particle size between about 1–100 microns, and the polymeric coating on the particles has a thickness in the range between about 0.1–20 microns.

17. A process in accordance with claim 1 wherein the deodorant ingredient is sodium or potassium bicarbonate or a mixture thereof.

18. A process in accordance with claim 1 wherein the deodorant ingredient is alkali metal bicarbonate containing up to about 30 weight percent of alkali metal carbonate, based on the weight of deodorant ingredient.

19. A process in accordance with claim 1 wherein between about 0.08–3 weight percent of a bacteriostat is included as an additional ingredient, based on the weight of cosmetic stick product.

20. A process in accordance with claim 1 wherein the polymer coating on the deodorant particles contains between about 0.5–40 weight percent of a water-insoluble polymer component.

21. A process for preparing an antiperspirant-deodorant cosmetic stick product which comprises (1) heating between about 10–50 parts by weight of a volatile silicone oil ingredient to a temperature of about 120°–220° F.; (2) adding to the heated silicone oil ingredient between about 1–30 parts by weight of a liquid emollient ingredient, between about 12–24 parts by weight of a low melting point wax ingredient, and between about 0.5–5 parts by weight of a surfactant ingredient to form a homogeneous fluid medium; (3) adding between about 18–30 parts by weight of a particulate antiperspirant ingredient to the heated fluid medium, wherein the surfaces of the added antiperspirant particles are pre-coated with a hydrophilic polymer; (4) adding between about 0.05–30 parts by weight of a particulate alkali metal bicarbonate deodorant ingredient to form a homogeneous fluid suspension medium; and (5) dispensing the heated fluid suspension medium into cosmetic stick containers, and cooling the container contents to form solid sticks at room temperature.

22. A process in accordance with claim 21 wherein the antiperspirant ingredient comprises between about 20–28 weight percent of the cosmetic stick product, and is a particulate solid having an average particle size between about 1–100 microns, and the polymeric coating on the particles has a thickness in the range between about 0.1–20 microns.

23. A process in accordance with claim 21 wherein the deodorant ingredient comprises between about 0.1–25 weight percent of the cosmetic stick product, and is a particulate solid having an average particle size between about 1–100 microns.

24. A process in accordance with claim 21 wherein the deodorant ingredient is sodium or potassium bicarbonate or a mixture thereof.

25. A process in accordance with claim 21 wherein the polymer coating on the antiperspirant particles contains between about 0.5–40 weight percent of a water-insoluble polymer component.

26. A process for preparing an antiperspirant-deodorant cosmetic stick product which comprises (1) heating between about 10–50 parts by weight of a volatile silicone oil ingredient to a temperature of about 120°–220° F.; (2) adding to the heated silicone oil ingredient between about 1–30 parts by weight of a liquid emollient ingredient, between about 12–24 parts by weight of a low melting point wax ingredient, and between about 0.5–5 parts by weight of a surfactant ingredient to form a homogeneous fluid medium; (3) adding between about 18–30 parts by weight of a particulate antiperspirant ingredient to the heated fluid medium, wherein the surfaces of the added antiperspirant particles are pre-coated with a hydrophilic polymer; (4) adding between about 0.05–30 parts by weight of a particulate alkali metal bicarbonate deodorant ingredient to form a homogeneous fluid suspension medium, wherein the surfaces of the added alkali metal bicarbonate particles are pre-coated with a hydrophilic organic polymer; and (5) dispensing the heated fluid suspension medium into cosmetic stick containers, and cooling the container contents to form solid sticks at room temperature.

27. A process in accordance with claim 26 wherein the antiperspirant ingredient comprises between about 20–28 weight percent of the cosmetic stick product, and is a particulate solid having an average particle size between about 1–100 microns, and the polymeric coating on the particles has a thickness in the range between about 0.1–20 microns.

28. A process in accordance with claim 26 wherein the deodorant ingredient comprises between about 0.1–25 weight percent of the cosmetic stick product, and is a particulate alkali metal bicarbonate solid having an average particle size between about 1–100 microns, and the polymeric coating on the particles has a thickness in the range between about 0.1–20 microns.

29. A process in accordance with claim 26 wherein the deodorant ingredient is sodium or potassium bicarbonate or a mixture thereof.

30. A process in accordance with claim 26 wherein the polymer coating on the antiperspirant and deodorant particles contains between about 0.5–40 weight percent of a water-insoluble polymer component.

* * * * *